US008357197B2

(12) United States Patent
McGraw et al.

(10) Patent No.: US 8,357,197 B2
(45) Date of Patent: Jan. 22, 2013

(54) PERCUTANEOUS SPINAL STABILIZATION DEVICE AND METHOD

(75) Inventors: J. Kevin McGraw, Columbus, OH (US); Dirk V. Hoyns, Conyers, GA (US)

(73) Assignee: Hatch Medical, L.L.C., Duluth, GA (US)

(*) Notice: Subject to any disclaimer, the term of this patent is extended or adjusted under 35 U.S.C. 154(b) by 1218 days.

(21) Appl. No.: 11/327,515

(22) Filed: Jan. 9, 2006

(65) Prior Publication Data
US 2006/0195094 A1 Aug. 31, 2006

Related U.S. Application Data

(63) Continuation-in-part of application No. 11/057,209, filed on Feb. 15, 2005.

(51) Int. Cl.
*A61F 2/44* (2006.01)

(52) U.S. Cl. .......... 623/17.11; 606/329; 606/86 R; 606/86 A

(58) Field of Classification Search .......... 606/258, 606/102, 246, 251, 254, 255, 262, 279, 99, 606/86 A, 104, 105, 62–68; 623/17.11
See application file for complete search history.

(56) References Cited

U.S. PATENT DOCUMENTS

| | | | |
|---|---|---|---|
| 1,630,239 A | 5/1927 | Binkley et al. | |
| 3,367,326 A | 2/1968 | Frazier | |
| 3,426,364 A | 2/1969 | Lumb | |
| 4,059,115 A | 11/1977 | Jumashev et al. | |
| 4,135,506 A | 1/1979 | Ulrich | |
| 4,169,470 A * | 10/1979 | Ender et al. | 606/62 |
| 4,773,402 A | 9/1988 | Asher et al. | |
| 4,790,303 A * | 12/1988 | Steffee | 606/300 |
| 4,834,757 A | 5/1989 | Brantigan | |
| 4,941,466 A * | 7/1990 | Romano | 606/80 |
| 5,133,716 A * | 7/1992 | Plaza | 606/250 |
| 5,179,915 A | 1/1993 | Cohen et al. | |
| 5,425,772 A | 6/1995 | Brantigan | |
| 5,439,464 A | 8/1995 | Shapiro | |
| 5,445,639 A | 8/1995 | Kuslich et al. | |
| 5,509,918 A | 4/1996 | Romano | |
| 5,527,316 A | 6/1996 | Stone et al. | |
| 5,639,237 A * | 6/1997 | Fontenot | 433/173 |
| 5,700,265 A | 12/1997 | Romano | |
| 5,735,899 A | 4/1998 | Schwartz et al. | |
| 5,792,044 A | 8/1998 | Foley et al. | |
| 5,899,908 A | 5/1999 | Kuslich et al. | |
| 5,928,267 A | 7/1999 | Bonutti et al. | |
| 6,056,749 A | 5/2000 | Kuslich | |
| 6,086,589 A | 7/2000 | Kuslich et al. | |
| 6,127,597 A | 10/2000 | Beyar et al. | |
| 6,175,758 B1 | 1/2001 | Kambin | |
| 6,241,769 B1 | 6/2001 | Nicholson et al. | |
| 6,258,090 B1 * | 7/2001 | Jackson | 606/916 |
| RE37,479 E | 12/2001 | Kuslich | |
| 6,530,929 B1 | 3/2003 | Justis et al. | |
| 6,558,386 B1 | 5/2003 | Cragg | |

(Continued)

FOREIGN PATENT DOCUMENTS

| | | |
|---|---|---|
| EP | 743045 | 11/1996 |
| WO | WO02/13732 | 2/2002 |

*Primary Examiner* — Eduardo C Robert
*Assistant Examiner* — Tara Carter
(74) *Attorney, Agent, or Firm* — Welsh Flaxman & Gitler LLC

(57) ABSTRACT

A system for the percutaneous stabilization of adjacent vertebrae includes a plurality of elongated stabilization devices. Each stabilization device includes a radius of curvature. Each stabilization device further includes a leading end and a trailing end wherein the leading end is pointed for penetration through a vertebral body.

23 Claims, 19 Drawing Sheets

U.S. PATENT DOCUMENTS

| | | |
|---|---|---|
| 6,575,979 B1 | 6/2003 | Cragg |
| 6,579,291 B1 * | 6/2003 | Keith et al. .................. 606/86 A |
| 6,607,530 B1 * | 8/2003 | Carl et al. ..................... 606/914 |
| 6,616,670 B2 | 9/2003 | Simon et al. |
| 6,638,276 B2 | 10/2003 | Sharkey et al. |
| 6,689,125 B1 | 2/2004 | Keith et al. |
| 6,805,697 B1 | 10/2004 | Helm et al. |
| 6,899,716 B2 | 5/2005 | Cragg |
| 6,921,403 B2 | 7/2005 | Cragg et al. |
| 6,923,811 B1 | 8/2005 | Carl et al. |
| 7,156,849 B2 | 1/2007 | Dunbar et al. |
| 7,160,300 B2 | 1/2007 | Jackson |
| 7,179,261 B2 | 2/2007 | Sicvol et al. |
| 7,909,871 B2 | 3/2011 | Abdou |
| 2001/0051807 A1 * | 12/2001 | Grafton ........................... 606/72 |
| 2002/0082598 A1 * | 6/2002 | Teitelbaum .................... 606/61 |
| 2002/0173796 A1 | 11/2002 | Cragg |
| 2003/0060826 A1 | 3/2003 | Foley et al. |
| 2003/0181913 A1 | 9/2003 | Lieberman |
| 2003/0229346 A1 | 12/2003 | Oribe et al. |
| 2003/0229347 A1 | 12/2003 | Sherman et al. |
| 2004/0082954 A1 | 4/2004 | Teitelbaum et al. |
| 2004/0210209 A1 | 10/2004 | Yeung et al. |

* cited by examiner

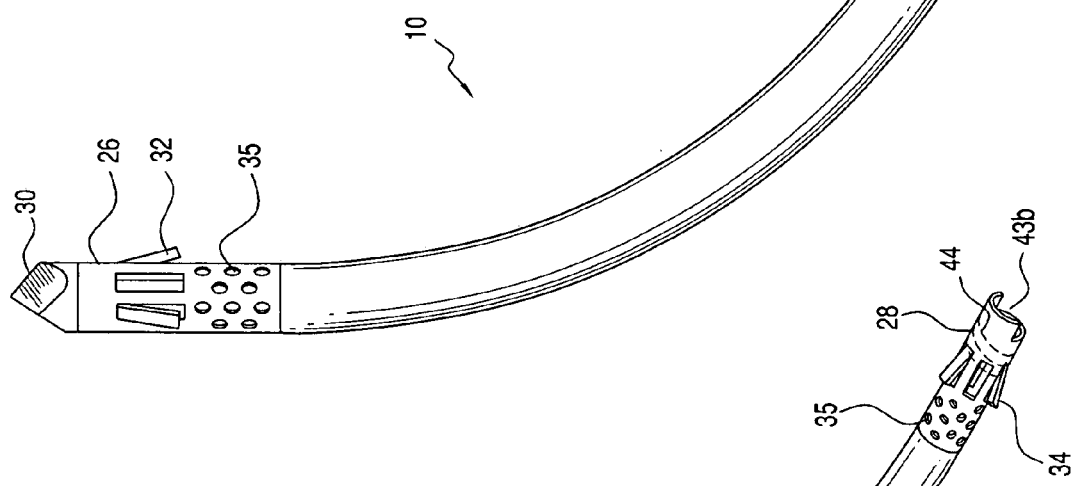
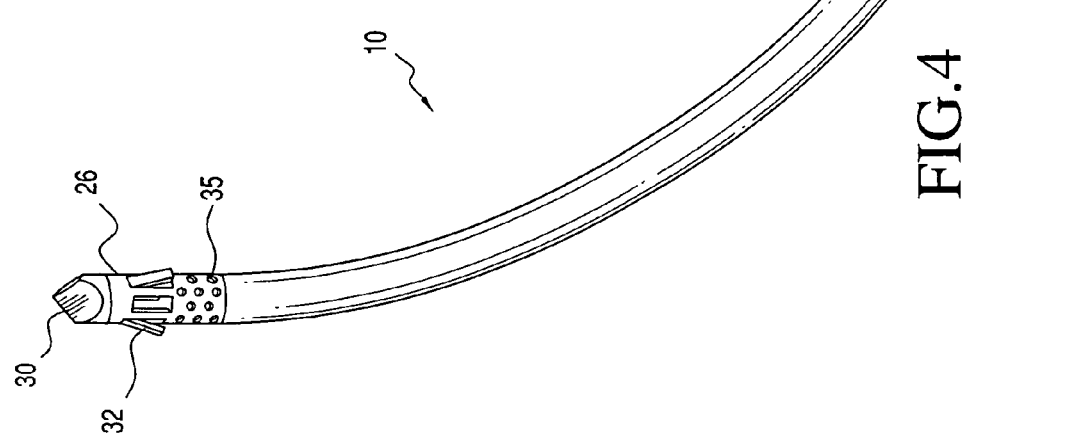

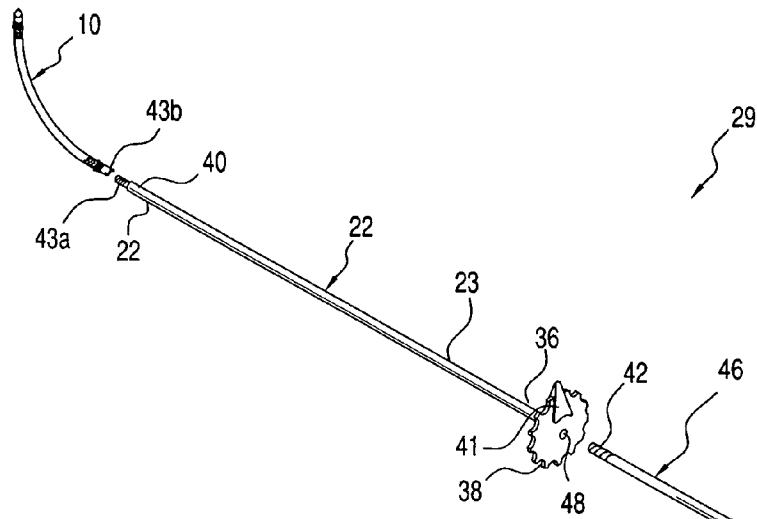
FIG.6
FIG.7
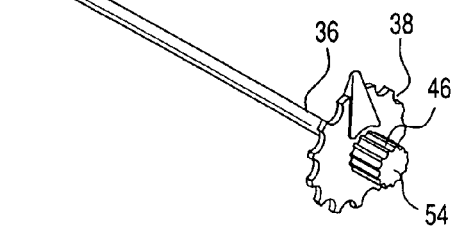

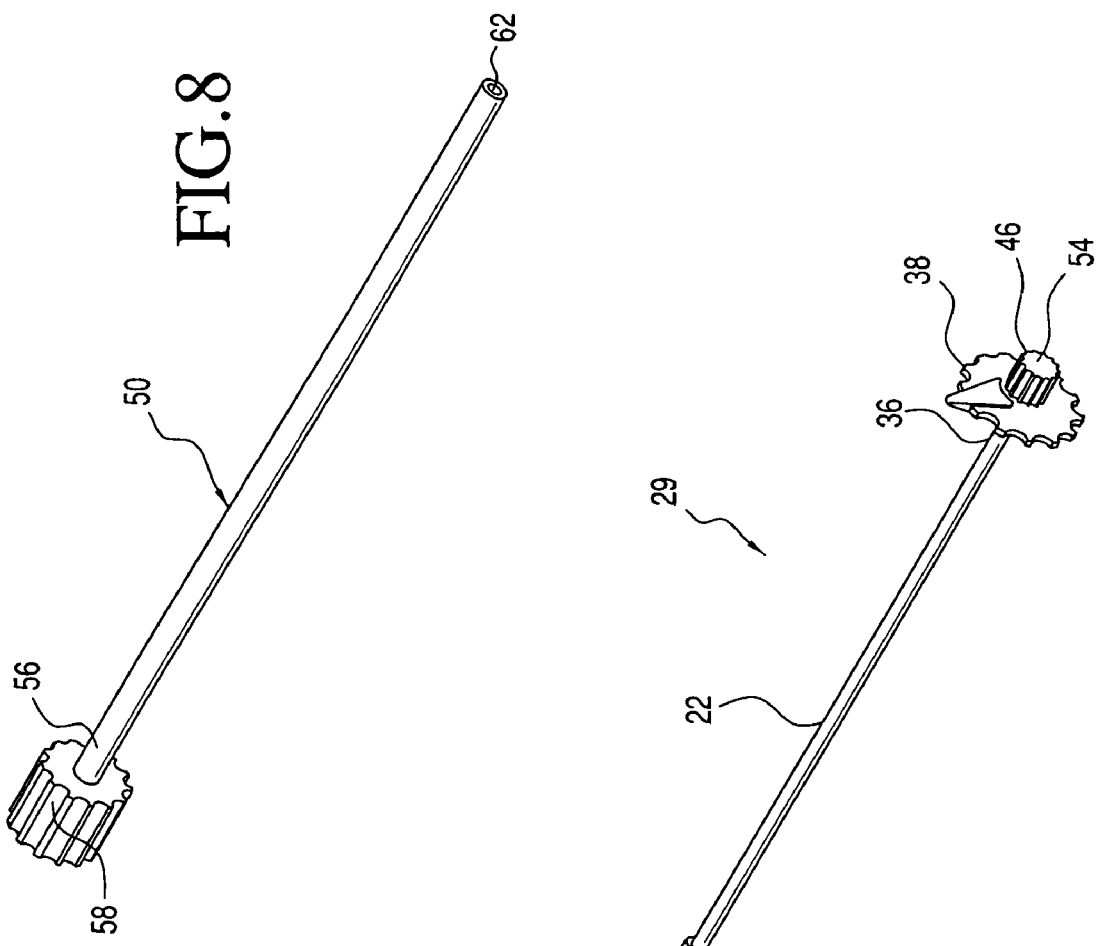

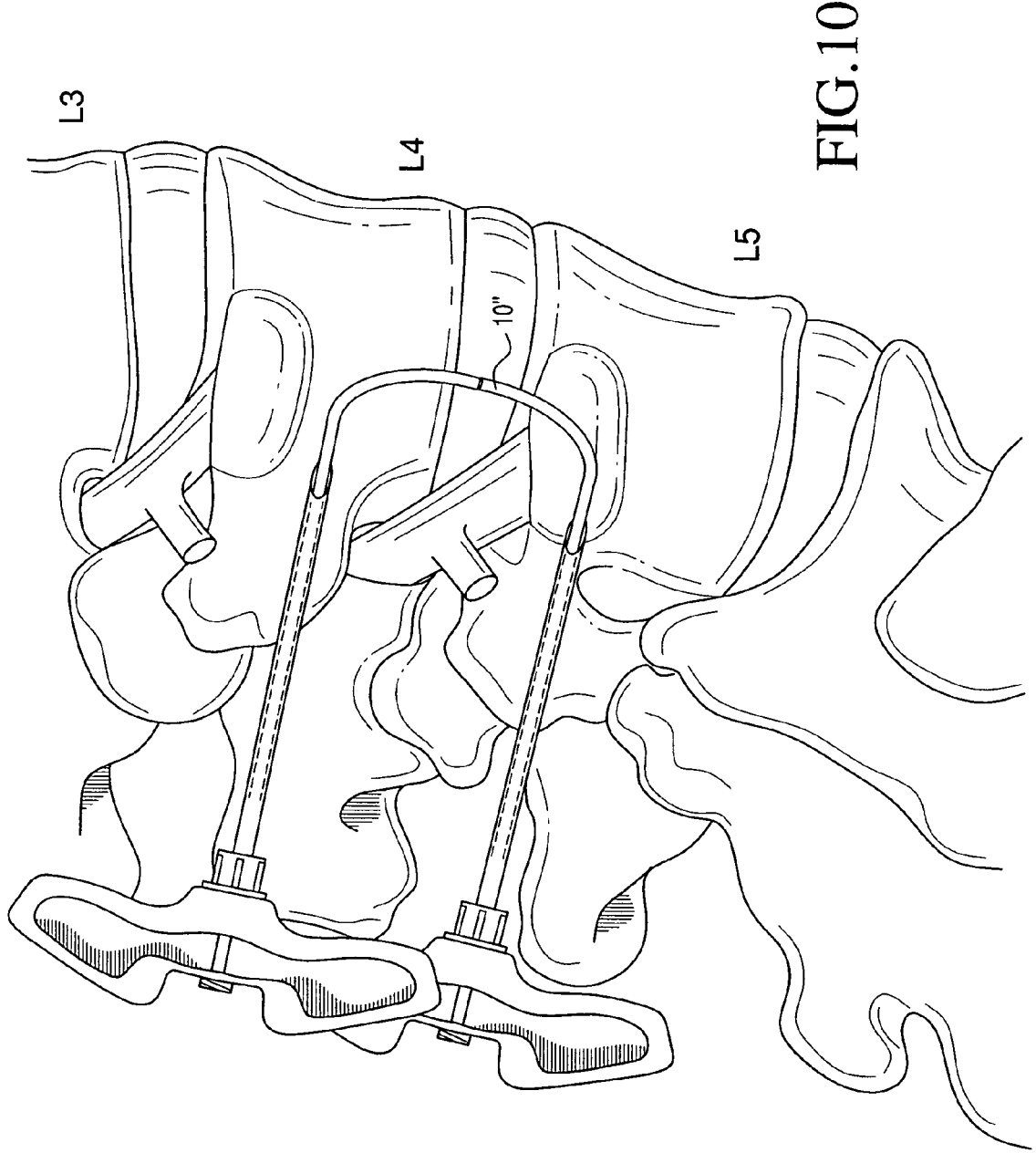

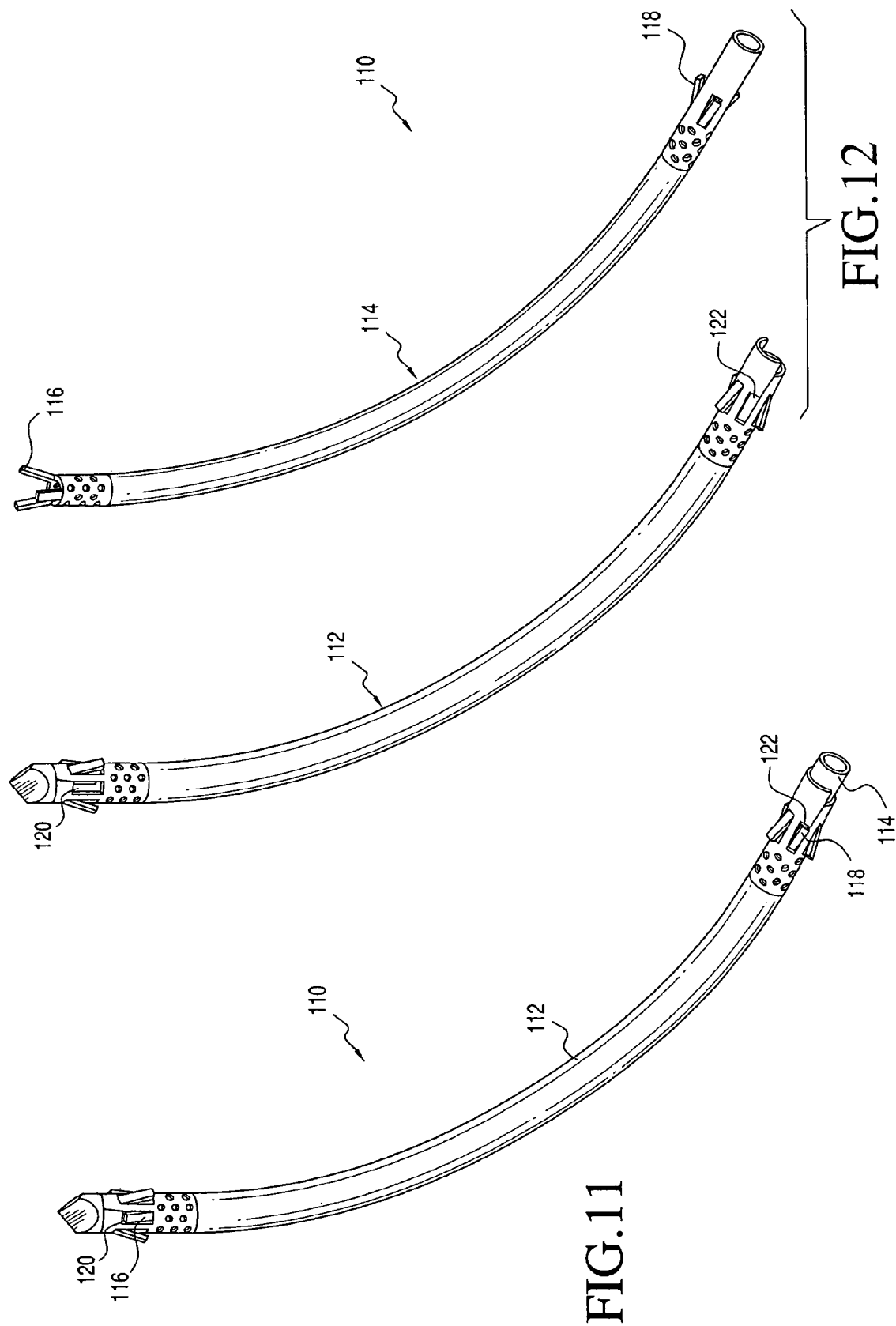

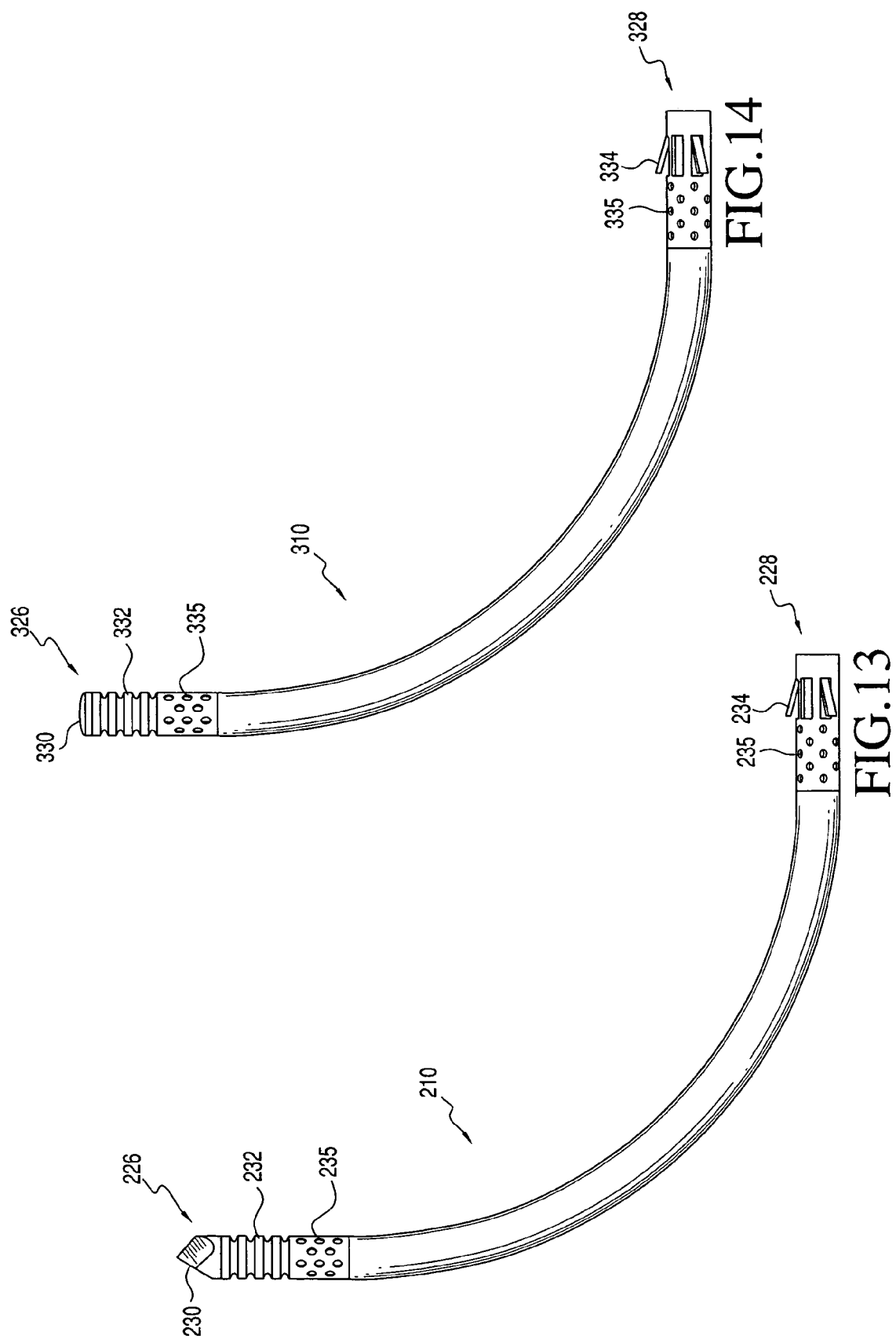

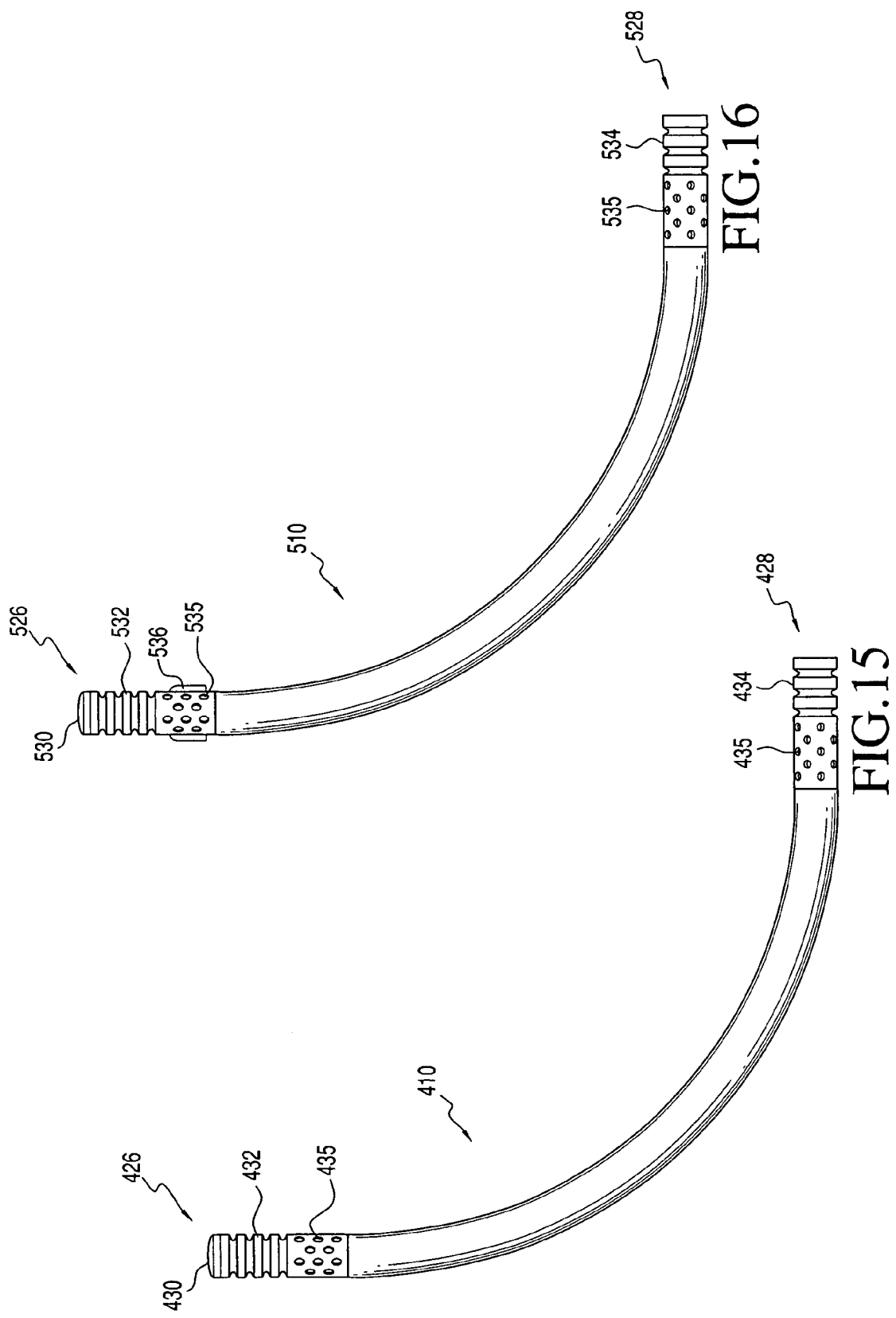

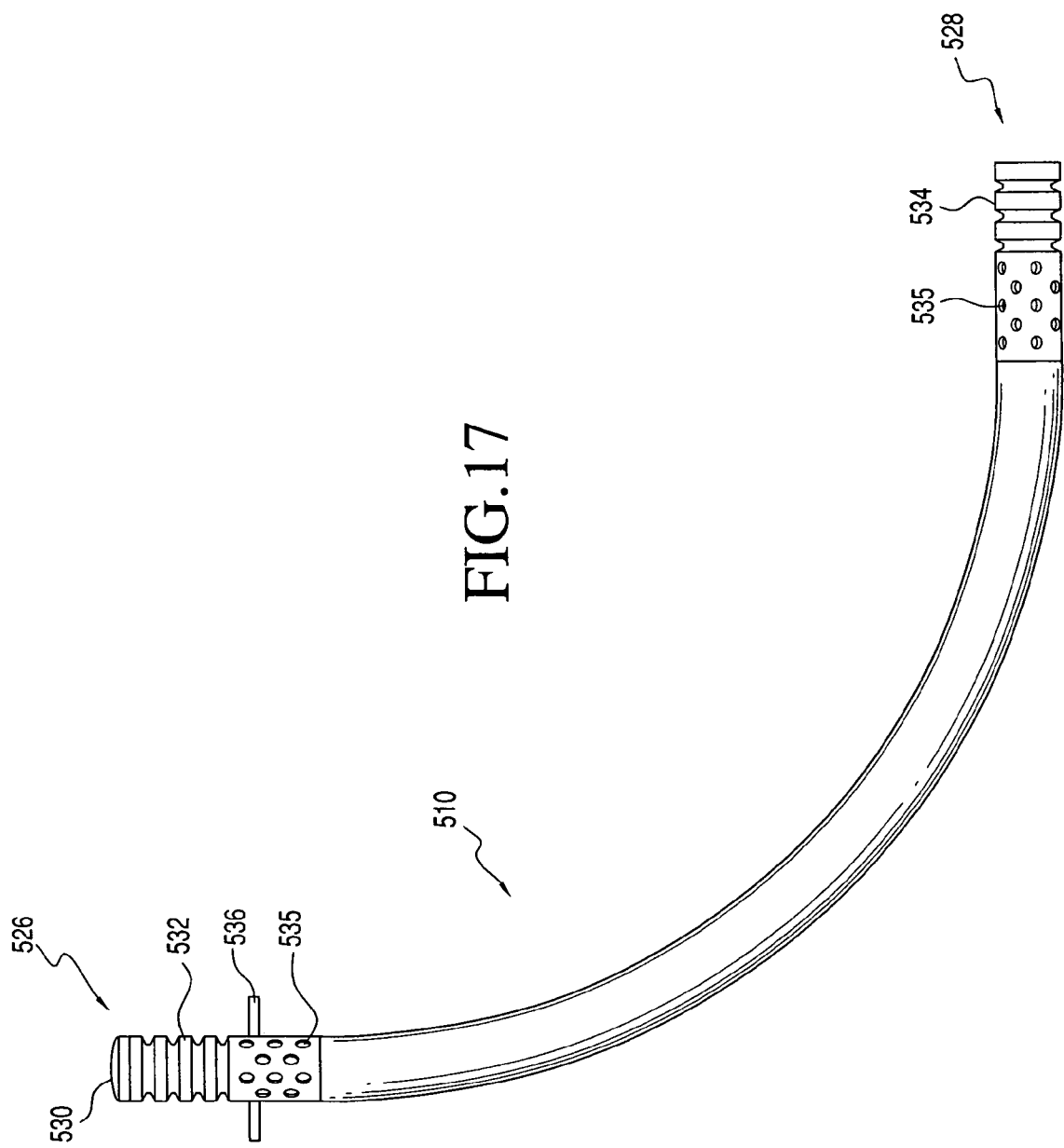

PERCUTANEOUS SPINAL STABILIZATION DEVICE AND METHOD

CROSS REFERENCE TO RELATED APPLICATIONS

This application is a continuation-in-part of U.S. patent application Ser. No. 11/057,209, filed Feb. 15, 2005, entitled "PERCUTANEOUS SPINAL STABILIZATION DEVICE AND METHOD", which is currently pending.

BACKGROUND OF THE INVENTION

1. Field of the Invention

The invention relates to a method and apparatus for percutaneous spinal stabilization. More particularly, the invention relates to a method and apparatus whereby a series of curved stabilization devices are employed in linking adjacent vertebrae.

2. Description of the Prior Art

It is often necessary to stabilize adjacent vertebrae. Various devices and methods for stabilizing the spinal column have been employed over the years. For example, plates and rods have been secured between adjacent vertebral bodies for the stabilization, or fixation, of the adjacent spinal bodies.

As those skilled in the art will certainly appreciate, the human spine is made up of 24 small bones, called vertebrae. The vertebrae protect and support the spinal cord. They also bear the majority of the weight put upon your spine. Vertebrae, like all bones, have an outer shell called cortical bone that is hard and strong. The inside is made of a soft, spongy type of bone, called cancerous bone.

The vertebral body is the large, round portion of bone. Each vertebra is attached to a bony ring. When the vertebrae are stacked one on top of the other, the rings create a hollow tube for the spinal cord to pass through. Each vertebra is held to the others by groups of ligaments. There are also tendons that fasten muscles to the vertebrae.

The bony ring attached to the vertebral body consists of several parts. The laminae extend from the body to cover the spinal canal, which is the hole in the center of the vertebrae. The spinous process is the bony portion opposite the body of the vertebra. There are two transverse processes (little bony bumps), where the back muscles attach to the vertebrae. The pedicle is a bony projection that connects to both sides of the lamina.

Although a variety of techniques for stabilizing adjacent vertebrae have been developed, many of these techniques involve highly invasive procedures. As recent developments within the surgical area have shown, minimally invasive surgical techniques are particularly desirable. These minimally invasive surgical techniques are well suited for application to procedures affecting the spine.

The development of percutaneous, minimally invasive spinal procedures has yielded major improvements in reducing recovery time and postoperative pain. These procedures require minimal, if any, muscle dissection and may be performed under local anesthetic. As a result, minimal tissue disruption is encountered.

With the foregoing in mind, a need continues for improvements in minimally invasive, percutaneous spinal stabilization techniques and apparatuses. The present invention provides such an improvement in percutaneous spinal stabilization.

SUMMARY OF THE INVENTION

It is, therefore, an object of the present invention to provide a system for the percutaneous stabilization of adjacent vertebrae. The system includes a plurality of elongated stabilization devices. Each stabilization device includes a radius of curvature. Each stabilization device further includes a leading end and a trailing end wherein the leading end is pointed for penetration through a vertebral body.

It is also an object of the present invention to provide a system including at least four stabilization devices.

It is another object of the present invention to provide a system wherein each of the stabilization devices is made of a shape memory or super elastic material.

It is a further object of the present invention to provide a system including an introducer needle shaped and dimensioned for penetration within the pedicles of vertebrae, wherein the introducer needle includes a lumen sized for the passage of the elongated stabilization devices therethrough.

It is still another object of the present invention to provide a system wherein an introducer rod is selectively secured to each of the stabilization devices at a respective trailing end thereof.

It is yet another object of the present invention to provide a system wherein threading respectively formed along the trailing end of each of the stabilization devices and the introducer rod releasably secures the stabilization devices to the introducer rod.

It is also an object of the present invention to provide a system wherein each of the stabilization devices includes barbs adjacent the trailing end for fixation with the vertebral body.

It is also an object of the present invention to provide a method for the percutaneous stabilization of adjacent vertebral bodies. The method is achieved by inserting an elongated stabilization device within the vertebrae such that it extends between adjacent vertebral bodies to securely stabilize the adjacent vertebral bodies.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 4 is a perspective view of a stabilization device in accordance with the present invention.

FIG. 5 is a side view of a stabilization device in accordance with the present invention.

FIG. 6 is an exploded view of the steering tube assembly.

FIG. 7 is a perspective view of the steering tube assembly.

FIG. 8 is a perspective view of the loading tube.

FIG. 9 is a perspective view of the steering tube assembly with the loading tube mounted over the stabilization device.

FIG. 10 is an alternate embodiment showing the utilization of a half circle configuration stabilization device.

FIG. 11 is a perspective view of a stabilization device in accordance with an alternate embodiment.

FIG. 12 is an exploded view of the components making up the stabilization device shown in FIG. 11.

FIGS. 13 through 17 disclose various embodiments of a stabilization device in accordance with the present invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limited, but merely as the basis for the claims and as a basis for teaching one skilled in the art how to make and/or use the invention.

Figure 1:
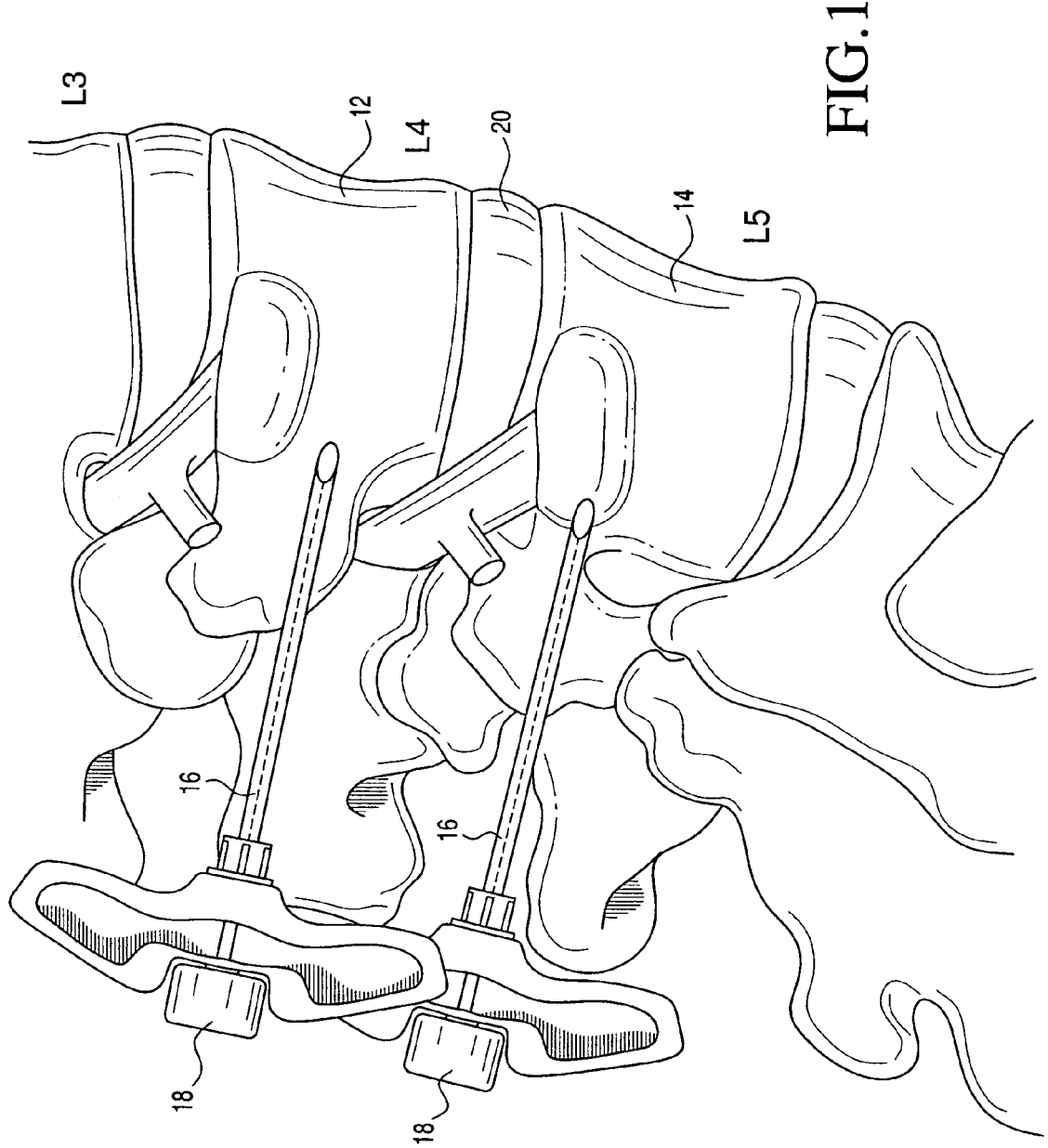
FIG. 1 is a perspective view showing the introducer needles inserted within the vertebral bodies.

With reference to the various figures, a stabilization device 10 and method for percutaneous spinal stabilization is disclosed. Generally, the stabilization device 10 is used in the stabilization of adjacent vertebral bodies 12, 14 and is inserted along the patient's posterior. The pedicles of the vertebral bodies 12, 14 to be stabilized are accessed with an introducer needle 16 positioned just beyond the posterior cortex of the vertebral bodies 12, 14 as shown in FIG. 1. As those skilled in the art will appreciate, it is contemplated pedicular access can also be achieved with a drill (hand or power) if needed.

Briefly, and as discussed below in greater detail, the introducer needle 16, in conjunction with its inner stylet 18, are first inserted into the pedicles of the vertebral bodies 12, 14 to be stabilized. They are advanced just beyond the posterior cortex of the vertebral bodies 12, 14. Once properly positioned, the inner stylet 18 of the introducer needle 16 is removed and a curved shape memory or super-elastic coring cannula (not shown) may be used to pre-drill a pilot channel for the stabilization devices 10, 10'. The coring cannula is removed, and the stabilization device 10, 10' is positioned proximal to the introducer rod 22.

Figure 2:
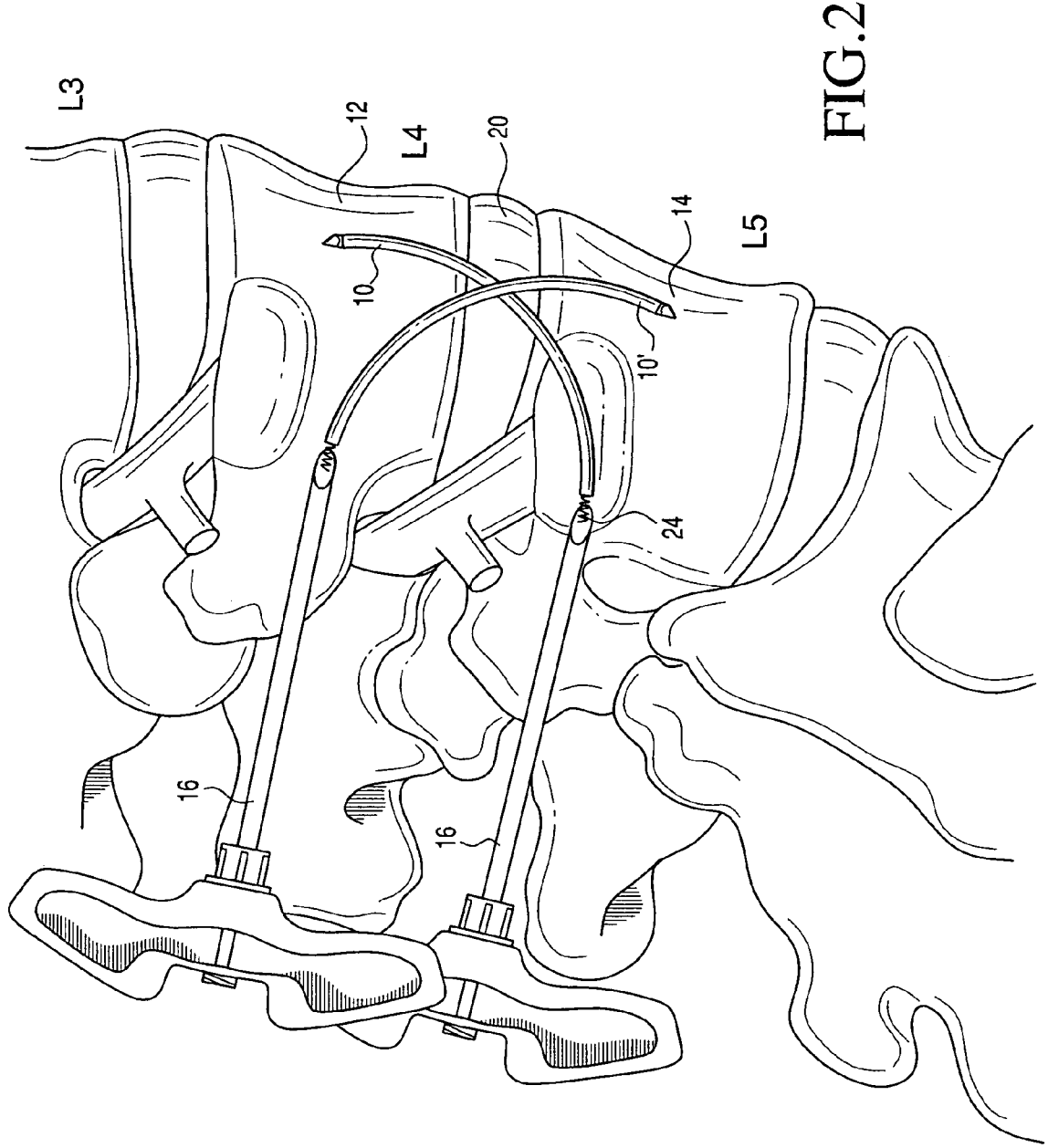
FIG. 2 is a perspective view showing the stabilization devices inserted within the vertebral bodies.

The stabilization device 10 is then advanced through the introducer needle 16 and into the vertebral bodies 12, 14 by passing it between adjacent vertebral bodies 12, 14 through the disc space 20 separating the adjacent vertebral bodies 12, 14. Once the first stabilization device 10 is positioned within and between the vertebral bodies 12, 14, a second stabilization device 10' is advanced from the upper vertebral body 12 to the lower vertebral body 14 forming a crisscross or curved "X" (see FIG. 2). In accordance with a preferred embodiment, the procedure is repeated on the contralateral side, producing a total of four stabilization devices 10, 10' used at each level to be stabilized.

Once the position of the stabilization devices 10, 10' is satisfactory, introducer rods 22 utilized in positioning the stabilization devices 10, 10' are removed and PMMA (polymethylmethacrylate) or other bone filler or bioadhesive (example cyanoacrylate) 24 is inserted to aid in the fixation of the leading ends 26 and trailing ends 28 of the stabilization devices 10, 10'.

Figure 3:
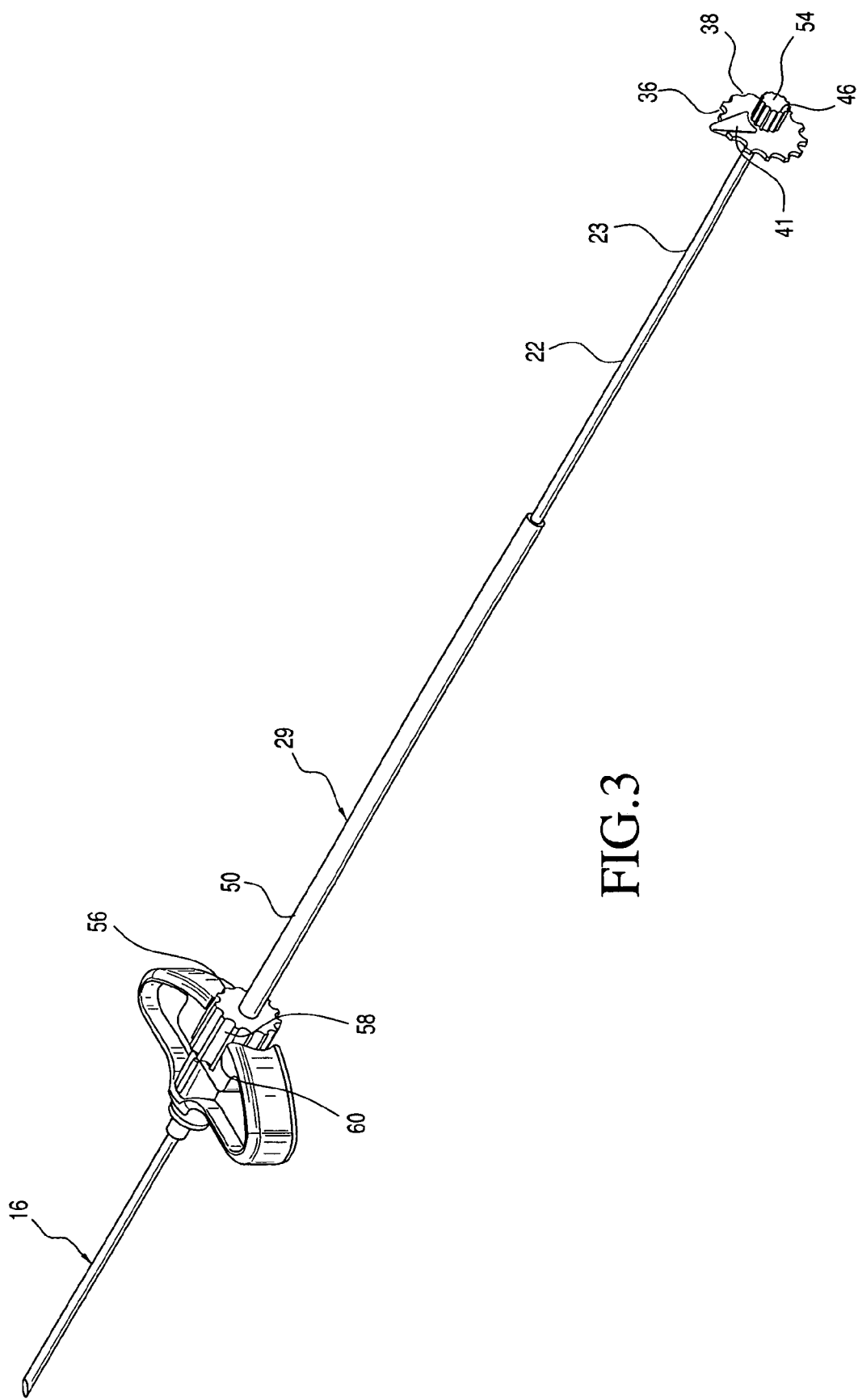
FIG. 3 is a perspective view of the introducer needle and steering tube assembly.
Figure 18:
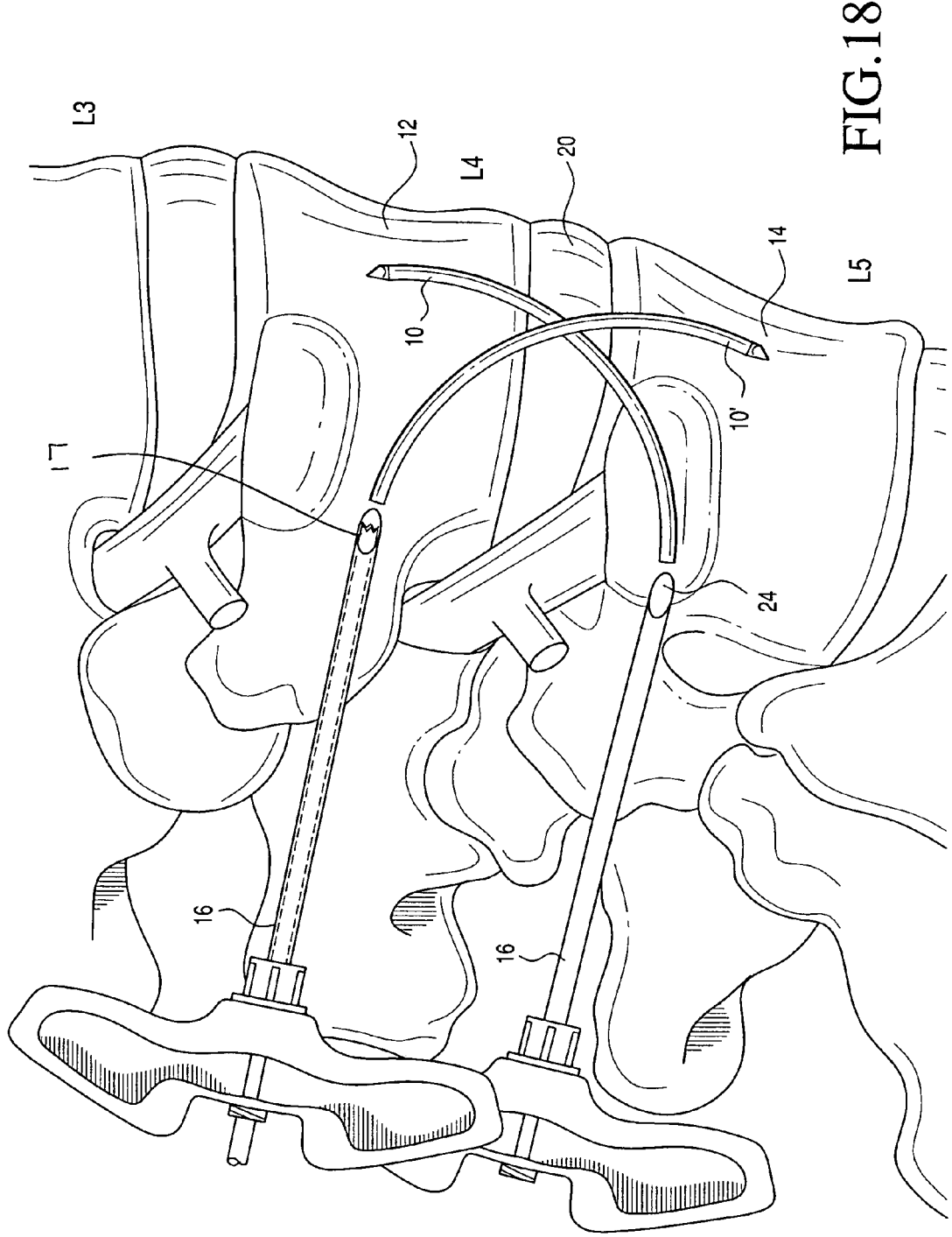
FIGS. 18 to 25 disclose procedures in accordance with the present invention.
Figure 19:
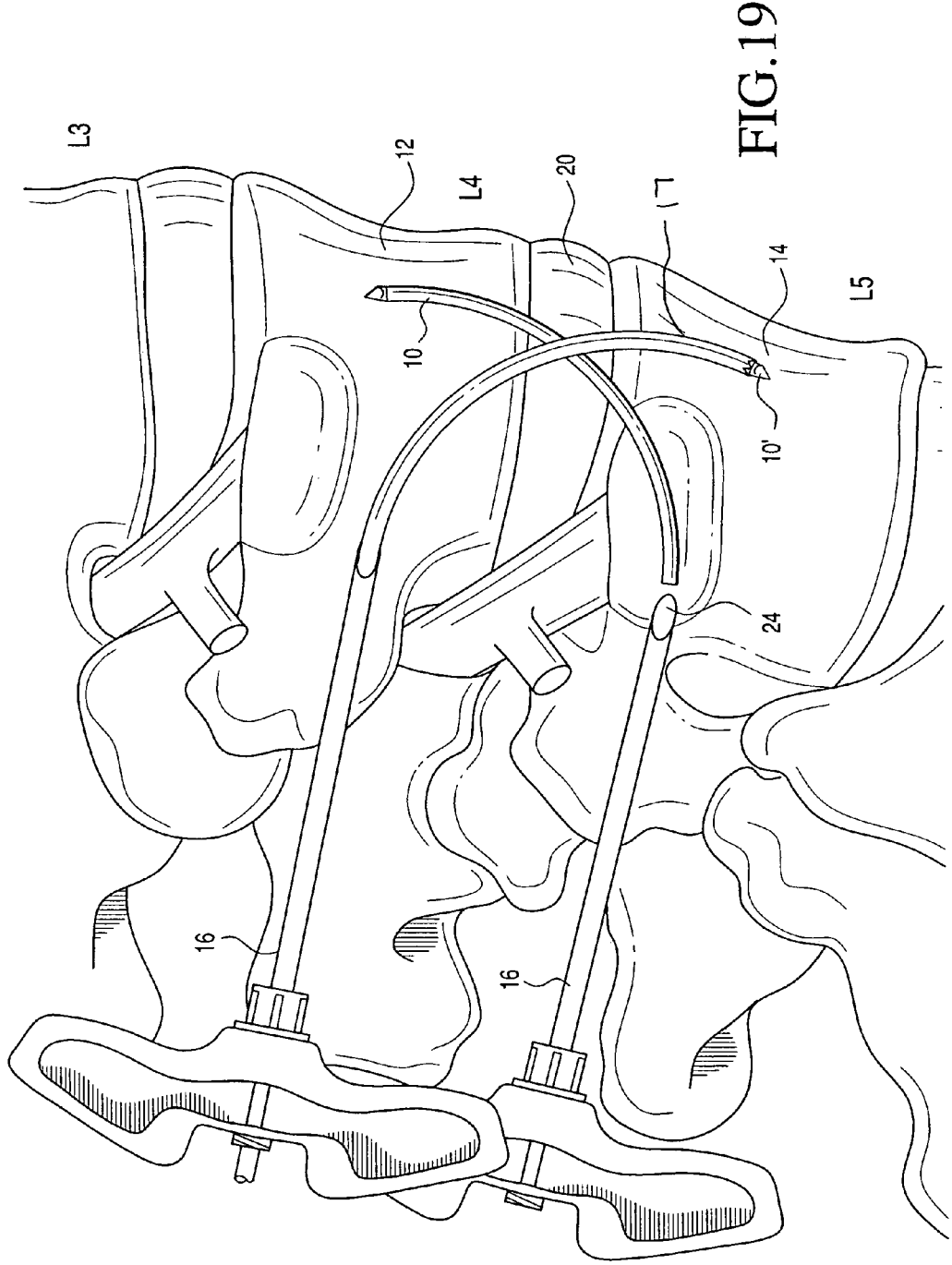
Figure 20:
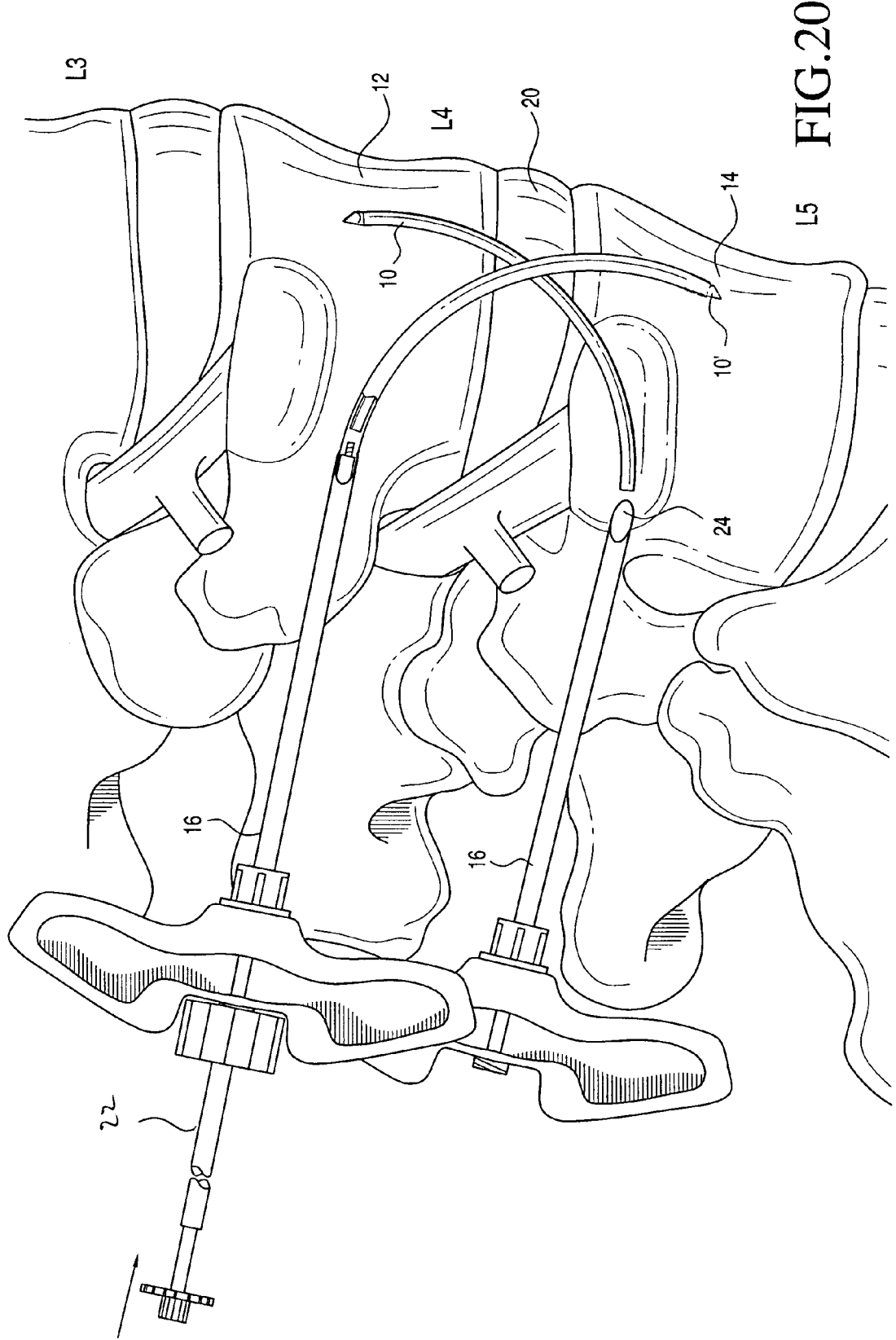
Figure 21:
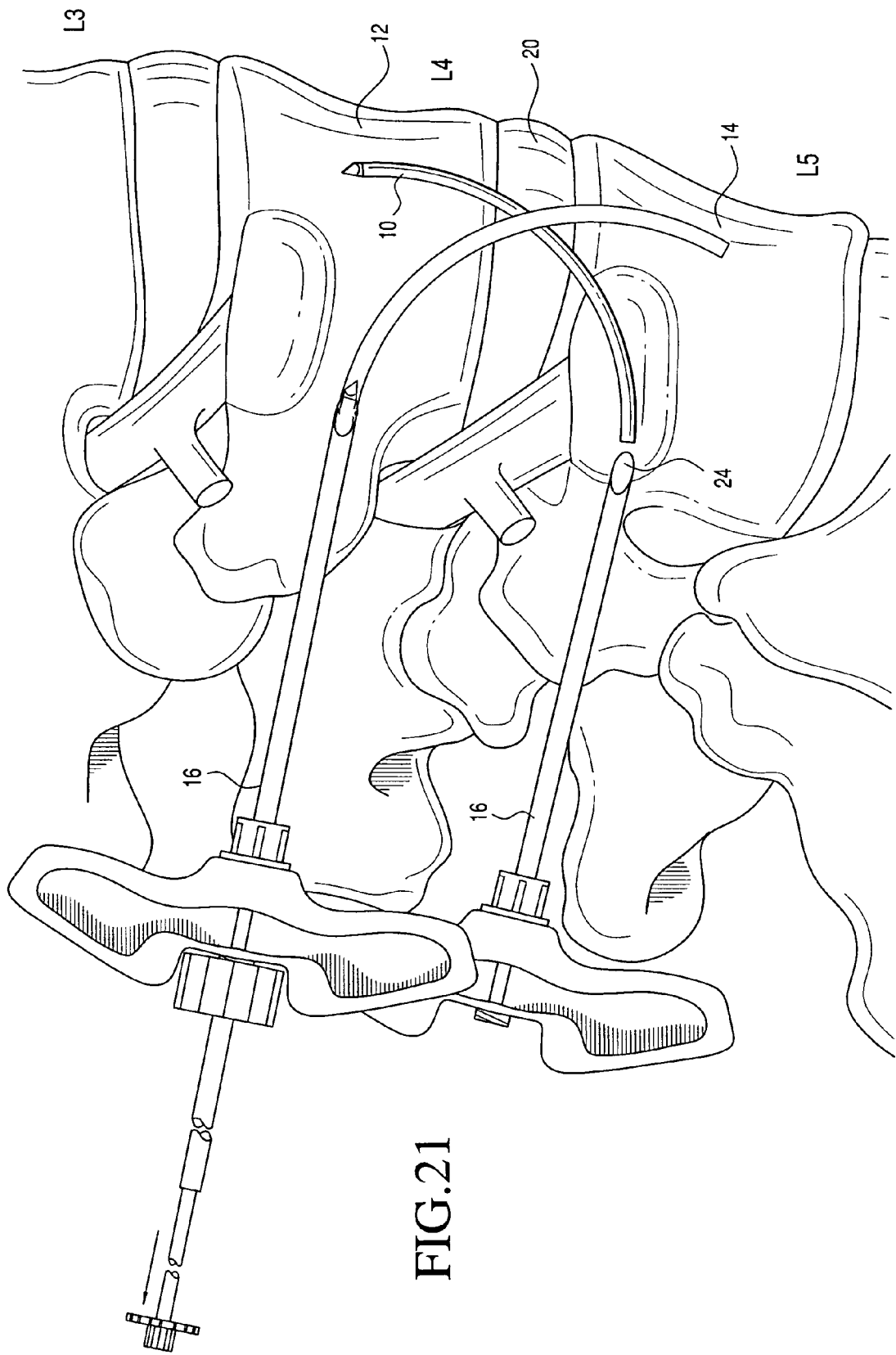
Figure 22:
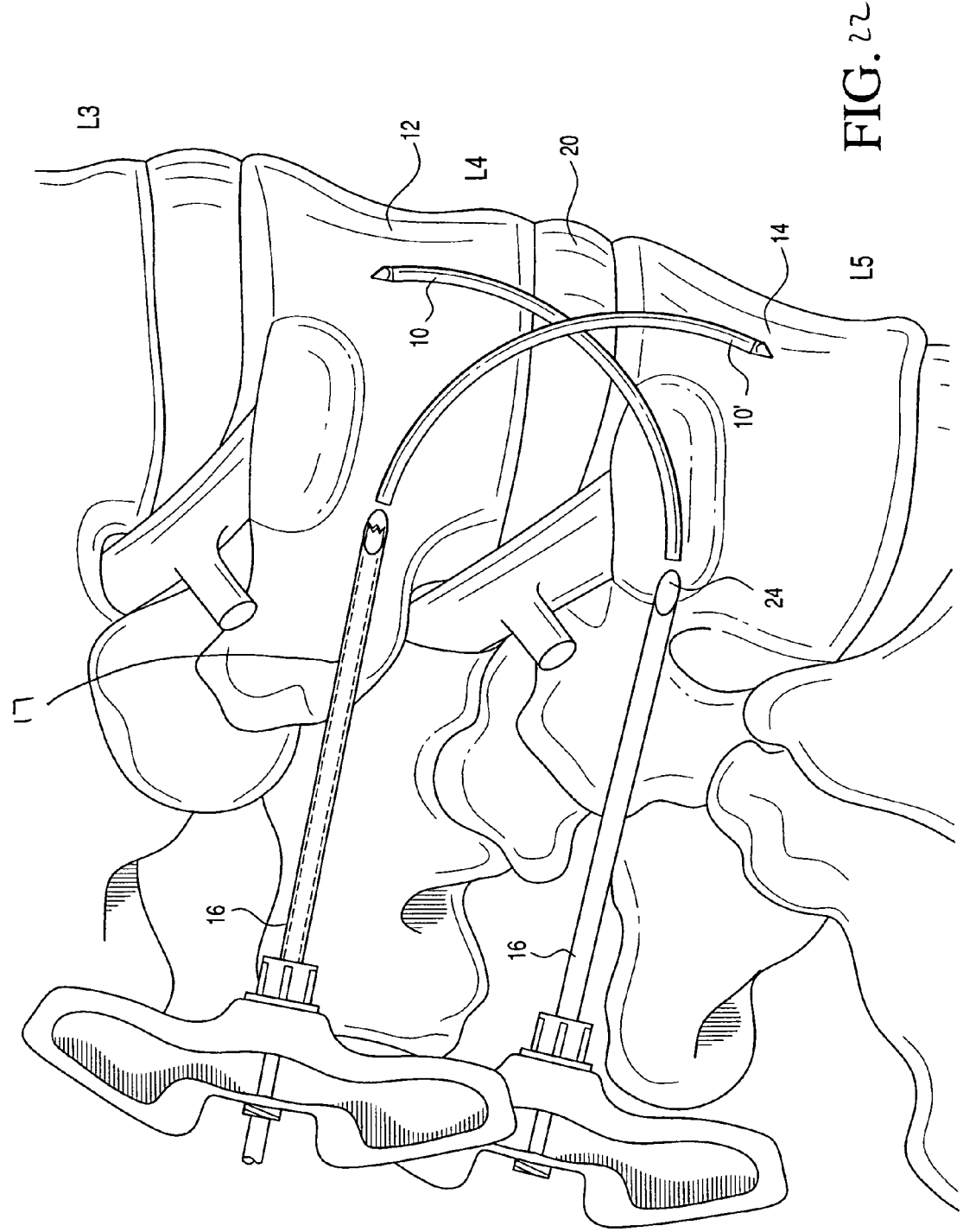
Figure 23:
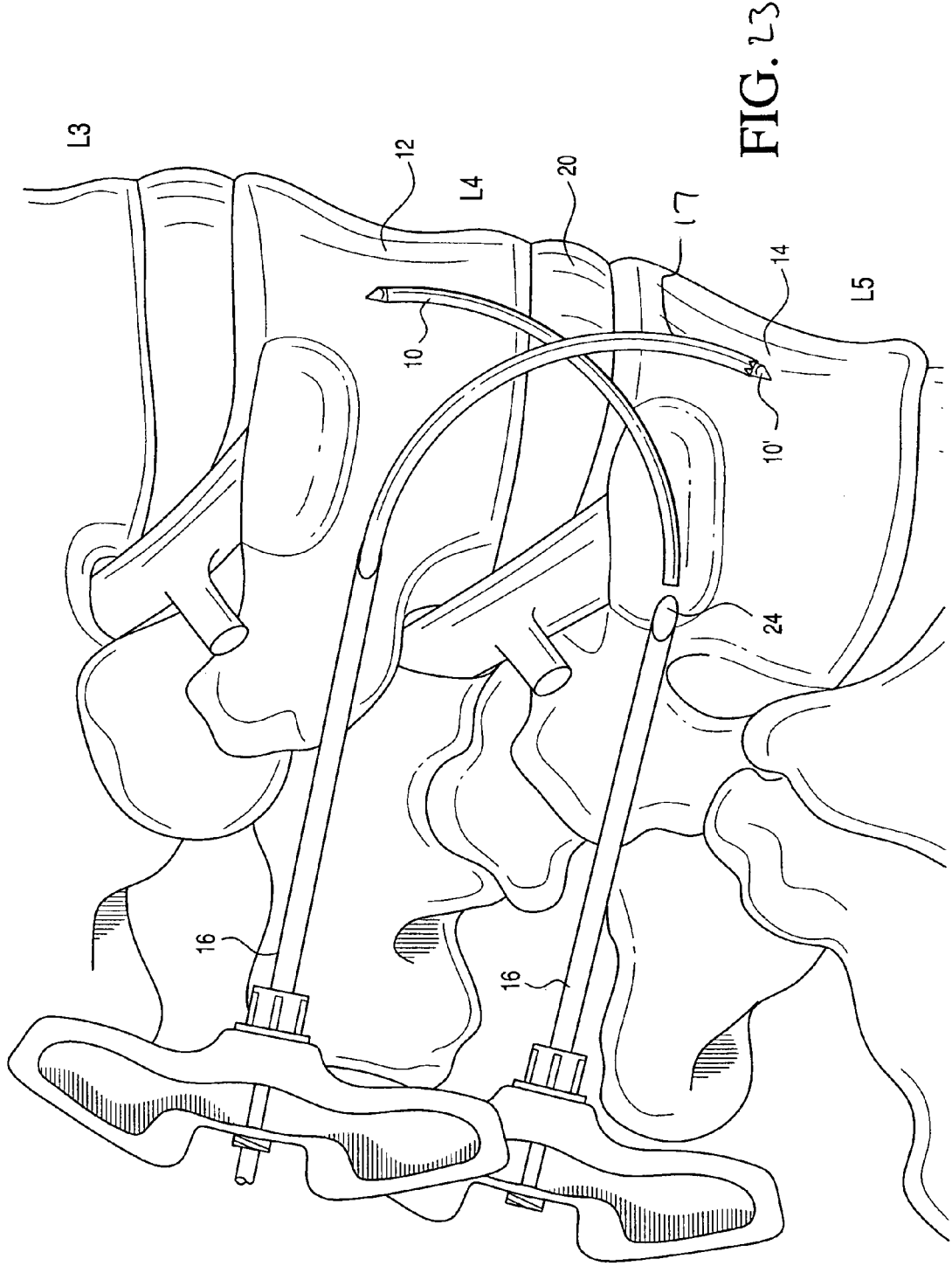
Figure 24:
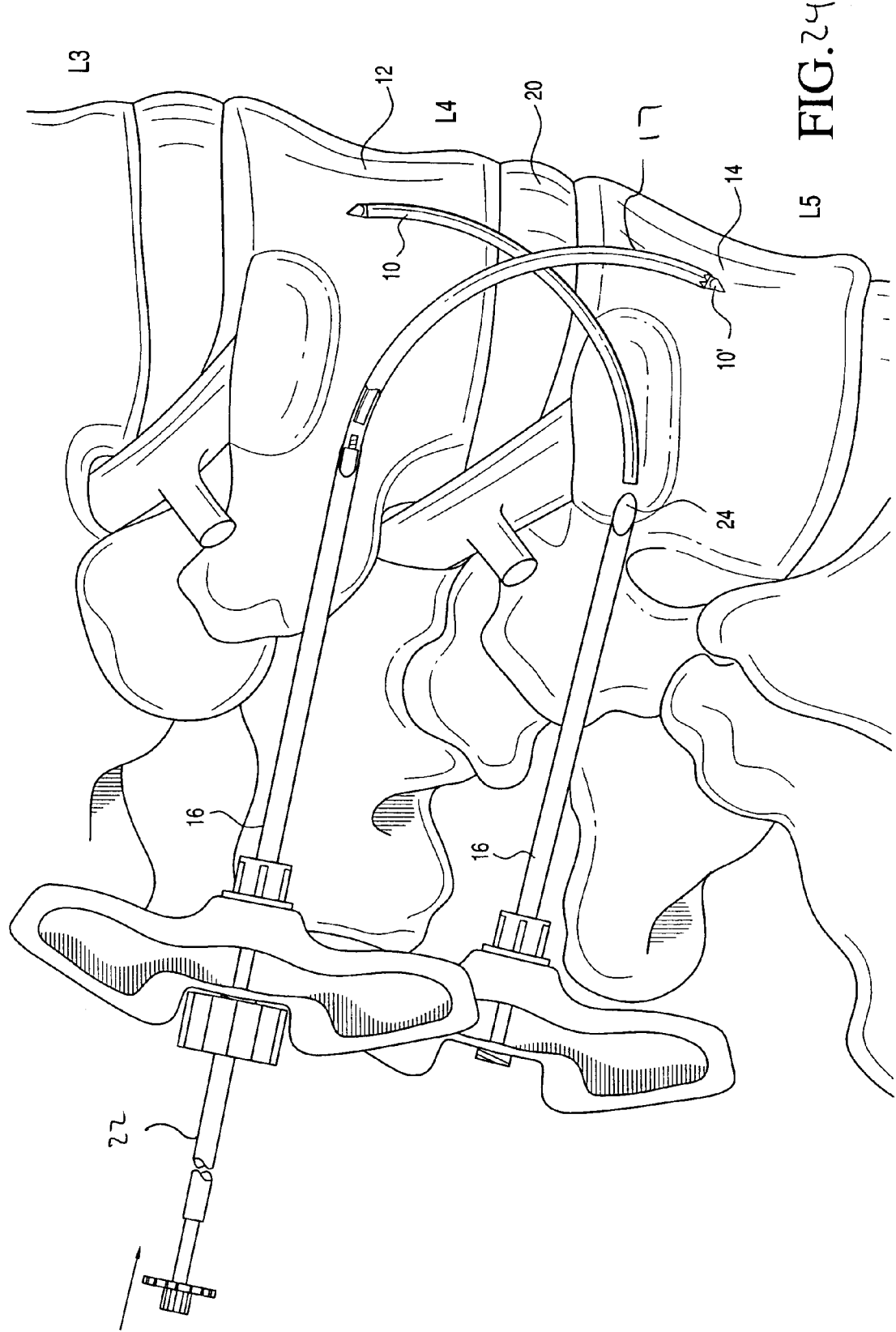
Figure 25:
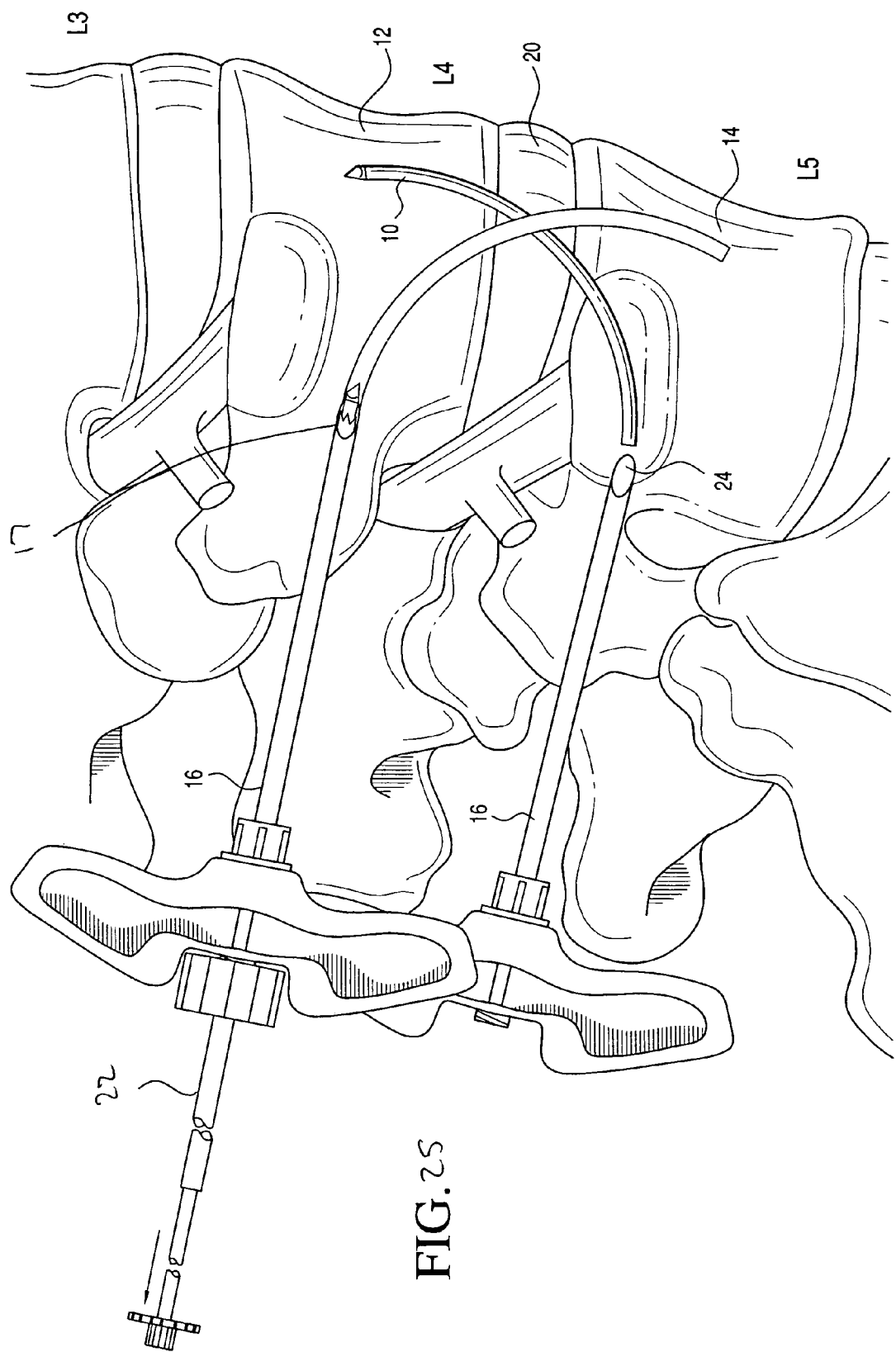

More particularly, and with reference to FIG. 3, the spinal stabilization system in accordance with the present invention employs a plurality of elongated stabilization devices 10, 10', an introducer needle 16 shaped and dimensioned for penetration within the pedicles of a vertebral body 12, 14 and a steering tube assembly 29, including an introducer rod 22, selectively secured to the various stabilization devices 10, 10'.

With regard to the stabilization devices 10, 10', only a first stabilization device 10 is described herein as those skilled in the art will appreciate that the other stabilization devices used in accordance with the present method are substantially identical. The stabilization device 10 is preferably made of solid, tubular or porous Nitinol, or other similar shape memory or superelastic materials. As a result, and as will be discussed below in greater detail, the stabilization device 10 is are substantially straight as it extends within the introducer needle 16 and only takes its desired curved configuration upon exiting the introducer needle 16 and entering the predetermined vertebral bodies 12, 14.

Referring to FIGS. 4 and 5, the elongated stabilization device 10 includes a leading end 26 and a trailing end 28. The leading end 26 is preferably configured with a sharp tip 30 such as a pencil, trocar or bevel point to facilitate passage through the vertebral bodies 12, 14 and barbs 32 to enhance secure positioning within the vertebral bodies 12, 14. Several ridges, or barbs 34, are also placed along the trailing end 28 to enhance secure positioning of the stabilization device 10 within the vertebral bodies 12,14. The barbs 32, 34 at the respective leading end 26 and trailing end 28 of the stabilization device 10 are formed to face in opposite directions, ensuring secure placement of the stabilization devices 10, 10' within the vertebral bodies 12, 14. Alternatively, and as shown in FIGS. 4 and 5, holes 35 could be placed on the leading and trailing ends 26, 28 of the stabilization device 10 to aid bony ingrowth or fixation with polymethylmethacrylate (PMMA), a bone filler or bioadhesive (example cyanoacrylate).

As briefly discussed above, the stabilization device 10 has a predetermined curved shape determined so as to provide the greatest contact between the adjacent vertebral bodies 12, 14. The elongated stabilization device 10 can come in variable lengths from 1 cm to 10 cm, predetermined by patient anatomy. The radius of curvature of the deployed stabilization device 10 can vary from 0.5 cm to 10 cm, more preferably, 3 cm to 6 cm, and the arc of the radius can encompass 10° to 240°, more preferably, 60° to 110°. While these parameters are disclosed in accordance with a preferred embodiment of the present invention, those skilled in the art will appreciate that variations are certainly possible without departing from the spirit of the present invention. For example, and with reference to FIG. 10, the stabilization device 10 may be formed in a C-shape or a complete semicircle.

It is contemplated the stabilization device might have a flexible point or articulation in a central region thereof to allow slight flexion within the disc space 20. The stabilization device 10 may also be formed in various lengths as will be determined by those skilled in the art.

As discussed above, the percutaneous spinal stabilization system further includes an introducer rod 22. Referring to FIGS. 3, 6, 7 and 9, the introducer rod 22 includes a first end 36 having a handle 38 and a second end 40. The handle 38 is formed with markings 41 providing users with orientation information when the stabilization device 10 is hidden from view during the installation procedure discussed below.

The introducer rod 22 includes a driver rod 46 that selectively extends through a lumen 48 in the introducer rod 22. The driver rod 46 includes a threaded end 42 shaped and dimensioned for engagement with a threaded cavity 44 formed within the trailing end 28 of the stabilization device 10. Although the introducer rod is disclosed as having a threaded cavity in accordance with a preferred embodiment of the present invention, the male and female components may be switched without departing from the spirit of the present invention.

Alignment of the stabilization device 10 with the introducer rod 22 is further enhanced by the provision of keying elements 43a, 43b at the second end 40 of the introducer rod 22 and the trailing end 28 of the stabilization device 10. This ensures that the introducer rod 22 is timed correctly with the direction of the arc described by the stabilization device 10 and allows for steering of the stabilization device 10 during placement. While a threaded connection with keying elements is disclosed in accordance with a preferred embodiment of the present invention, it is contemplated other attachment structures may be employed without departing from the spirit of the present invention.

The shaft 23 of the introducer rod 22 is preferably formed from stainless steel and the handle 38 is formed of hard steel such that it may be struck with a hammer to aid in insertion of the stabilization device 10. However, those skilled in the art will appreciate that other materials may be used without departing from the spirit of the present invention.

The trailing end 28 of the stabilization device 10 is keyed 43b and threaded 44 for engagement within the threaded end 42 formed at the end of the driver rod 46. As such, and as will be discussed below in greater detail, once the stabilization device 10 is properly positioned between the vertebral bodies 12, 14, the integral threaded driving rod 46 within the lumen 48 of the introducer rod 22 may be simply rotated, for example, in a counterclockwise manner, to release the stabilization device 10. As such, the introducer rod 22 is provided with a directional arrow 41 on the handle 38 at its first end 36 to indicate the direction of curvature of the stabilization device 10 and the desired rotation for deployment of the stabilization device 10.

The introducer rod 22 (including the driver rod 46) functions in conjunction with a loading tube 50 to create the steering tube assembly 29 used during placement of the stabilization device 10 in accordance a preferred embodiment of the present invention. As mentioned above, the driver rod 46 is shaped and dimensioned for placement within the lumen 48 extending from the first end 36 of the introducer rod 22 to the second end 38 of the introducer rod 22. The driver rod 46 is placed within the lumen 48 of the introducer rod 22 during the installation procedure and is threadingly coupled to the stabilization device 10. The driver rod 46 also acts as a stabilizing structure while the steering tube assembly 29 is struck during installation. With this in mind, the driver rod 46 is formed with a head member 54 shaped and dimensioned such that it may be rotated during coupling and uncoupling, or struck by a hammer or other surgical instrument during installation in accordance with the present invention.

Since the stabilization device 10 is formed to assume an arced shaped once installed within the vertebral body, the loading tube 50 is provided to assist in the loading of the stabilization device 10 and introducer rod 22 within the introducer needle 16. Referring to FIGS. 3, 8 and 9, the loading tube 50 includes a first end 56 with a notched head 58 shaped and dimensioned for keyed placement within a recess 60 formed in the introducer needle 16. The loading tube 50 further includes a lumen 62 extending its entire length for passage of the stabilization device 10 and introducer rod 22 therethrough during the installation process.

With regard to the introducer needle 16, it is shaped and dimensioned for penetration within the pedicles of the vertebral bodies 12, 14. As with other known introducer needles, the introducer needle 16 will include a central stylet 18 that may be removed once proper positioning of the introducer needle 16 is achieved. The introducer needle 16 includes a lumen sized for the passage of the elongated stabilization device 10 and the introducer rod 22 therethrough. For example, it is contemplated that a 10 or 11 gauge needle 16 will be sufficient for the purposes of the present invention, although those skilled in the art will appreciate that other sizes could be used without departing from the spirit of the present invention.

Alternatively, an introducer needle could be used to reach the cortex of the pedicle. The inner stylet would then be removed and a guide wire (k-wire) placed inside the needle lumen. The needle would then be removed, leaving the guide wire. A drill (hand or power) could then be advanced over the wire guide. Pedicular access would then be obtained by drilling into the pedicle just beyond the posterior cortex of the vertebral body. The drill would then be removed over the wire guide and then a cannula would then be advanced over the wire guide. The cannula is for passage of the stabilization device as described.

The steering tube assembly 29 and introducer needle 16 are assembled in the following manner for use in accordance with the present invention. The stabilization device 10 is first positioned within the loading tube 50 and the introducer rod 22 is then passed within the lumen 62 of the loading tube 50 and engaged with the stabilization device 10 by threading the driving rod 46 and the stabilization device 10 together. Because of the keying elements 43a, 43b on the trailing end 28 of the stabilization device 10 and the second end 40 of the introducer rod 22, as well as the marking 41 on the handle 38 of the introducer rod 22, orientation of the stabilization device 10 is always known despite the fact it is hidden within the loading tube 50.

Thereafter, the head 58 of the loading tube 50 is installed within the recess 60 of the introducer needle 16. The assembly is now ready for use in the placement of a stabilization device 10 within the vertebral body 12, 14 of a patient.

It is contemplated that the loading of the present assembly may be varied through the removal of the loading tube prior to completion of the assembly. It is believed this technique would slightly reduce the length of the assembly. More particularly, the stabilization device is positioned within the loading tube as discussed above. However, the stabilization device/loading tube is then mounted upon the introducer needle and the stabilization device is moved within the needle. Thereafter, the loading tube is removed, the introducer rod is secured to the stabilization device (while it sits within the introducer needle) and the driver rod is placed within the lumen of the introducer rod.

As briefly discussed above, percutaneous spinal stabilization in accordance with the present invention is achieved by first inserting the introducer needles 16 within the pedicles of the vertebral bodies 12, 14 to a position just beyond the posterior cortex of the vertebral bodies 12, 14 into which the stabilization devices 10, 10' are to be positioned. Positioning as discussed below is monitored through the use of real time imaging technology. It is preferred that all four introducer needles 16 are inserted initially, followed by placement of the stabilization devices 10, 10'. However, the specific approach adopted by individual practitioners may vary depending upon specific preferences.

As discussed above, the following procedure is preferably repeated four times, creating a criss-cross pattern between adjacent verterbral bodies 12, 14. However, the procedure will only be discussed herein once, as those skilled in the art will understand how to create the appropriate criss-crossing arrangement by inserting stabilization devices 10, 10' into both the upper and lower vertebral bodies 12, 14.

Once the introducer needle 16 is properly positioned, the inner stylet 18 of the introducer needle 16 is removed and a curved shape memory or super elastic coring cannula (not shown) may be used to pre-drill a pilot channel for the stabilization device 10. The coring cannula is then removed, and the stabilization device 10 is positioned distal to the introducer rod 22. Alternatively, the stabilization device 10 may be used independently without the curved coring needle described herein.

The stabilization device 10, with the introducer rod 22 secured and keyed to its trailing end 28, is forced through the introducer needle 16 under the control of the introducer rod 22, into the upper vertebral body 12, through the upper vertebral body 12 and into the lower vertebral body 14 such that approximately half of the stabilization device 10 is positioned within the upper vertebral body 12 and half is positioned within the lower vertebral body 14. As discussed above, this procedure is repeated for each of the stabilization devices 10, 10' to be deployed with two stabilization devices 10, 10' entering the lower vertebral body 14 and extending toward the upper vertebral body 12 and two stabilization devices 10 entering the upper vertebral body 12 and extending toward the lower vertebral body 14. More particularly, and with reference to FIG. 2, the stabilization devices 10, 10' are positioned within the vertebral bodies 12, 14 such that they criss-cross when viewed in both a lateral view and a frontal view.

Once the stabilization device 10 is properly positioned, the introducer rod 22 is removed by simply twisting the integral threaded driver rod 46 positioned within the lumen 48 of the introducer rod 22 in a counterclockwise direction to thereby unscrew and uncouple the second end 40 of the introducer rod 22 from the trailing end 28 of the stabilization device 10. Thereafter, adhesive or bone filler is forced within the aperture created by, or through the center of the stabilization device 10. For example, polymethylmethacrylate (PMMA) is injected into the vertebral bodies 12, 14 through the introducer needle 16 to aid in fixation. Small holes can be placed in the leading and trailing ends of the stabilization device to further facilitate bony ingrowth. Alternatively, the stabilization device may be made of a porous material and coated with an osteoconductive substance (for example bone morphogenetic protein), or a combination thereof. Also, instead of injecting PMMA to facilitate device fixation, a synthetic cortical bone void filler, such as beta tricalciumphosphate or bioadhesive (example cyanoacrylate) may also be employed.

In accordance with an alternate embodiment of the present invention, it may be desirable to have the stabilization device preloaded into a cartridge. The pedicles of the vertebral bodies to be stabilized are accessed with a 9 or 10 gauge introducer needle. A curved Nitinol introducer needle is advanced through the first needle from the vertebral body below across the disc space to be stabilized to the vertebral body above. Likewise, a second curved needle is advanced from the vertebral body above to the vertebral body below, forming a cross. The stabilization device (preloaded into an introducer cartridge) is inserted into the curved needle. A push rod is used to advance the stabilization device to the end of the curved needle. The device is now positioned across the disc space to be stabilized. Holding the push rod stationary, the curved needle is retracted uncovering the stabilization device. The device is now positioned across the disc space. Likewise, a second device is deployed in a similar fashion through the other curved needle forming a cross. The procedure is repeated on the contralateral hemivertebrae. A total of four devices can be used. PMMA, bone filler or bioadhesive (example cyanoacrylate) can then be inserted to aid in device fixation. It is possible that adequate stabilization can be achieved by inserting only two devices, one from each hemivertebrae.

Another method of spinal stabilization with the present stabilization device involves insertion of a 9 or 10 gauge needle into the pedicles (four) of the vertebral bodies to be stabilized. A curved needle is then advanced to the disc space to be stabilized. A second curved needle is advanced to the disc space from the vertebral body above. The two curved needle tips are advanced until they meet in the disc space. The stabilization device (preloaded into an introducer cartridge) is inserted into one of the curved needles. A push rod is used to advance the stabilization device through the first needle and into the second needle across the disc space. The device will resemble a half circle or C-shape across the disc space. Holding the push rod stationary, one curved needle is retracted uncovering one half of the stabilization device. The push rod is then inserted into the other curved needle. Holding the push rod stationary, the second curved needle is retracted uncovering the second half of the device. The device is now positioned across the disc space. The procedure is repeated on the contralateral side. Likewise, PMMA, bone filler bioadhesive can be inserted to aid in fixation.

In accordance with yet a further embodiment of the present invention, and with reference to FIGS. 11 and 12, a coaxial stabilization device 110 design is disclosed. The coaxial stabilization device 110 includes an outer stabilization member 112. The outer stabilization member 112 is sized and dimensioned for insertion in the manner described above with reference to the prior embodiment.

The coaxial stabilization device 110 includes a secondary, or inner, stabilization member 114 timed and inserted coaxially inside the outer stabilization member 112. The secondary stabilization member 114 is pushed within the outer stabilization member 112 after it is positioned within the vertebral bodies and is installed in a manner substantially as described above with reference to the first embodiment.

Once in place, reverse-facing barbs 116, 118 formed on the secondary stabilization member 114 lock into the clearance holes 120, 122 in the proximal and distal ends of the outer stabilization member 112, thereby preventing movement in both directions, as could happen if the vertebra were moved in compression or tension.

The coaxial arrangement would double the wall thickness of the stabilization device, allowing for easier introduction of the device due to the two thinner walls, and subsequently reduce bending force. If flexibility is desired in the implant, this could be varied by using different wall thicknesses to fine tune the bending force.

Referring to FIG. 13, yet another embodiment of a stabilization device in accordance with the present invention is disclosed. As with the prior embodiments, the stabilization device 210 is preferably made of solid, tubular or porous Nitinol, or other similar shape memory or superelastic materials. As a result, the stabilization device 210 is substantially straight as it extends within the introducer needle and only takes its desired curved configuration upon exiting the introducer needle and entering the predetermined vertebral bodies.

The stabilization device 210 includes a leading end 226 and a trailing end 228. The leading end 226 is preferably configured with a sharp tip 230 such as a pencil, trocar or bevel point to facilitate passage through the vertebral bodies. The leading end 226, just proximal to the tip 230, includes a series of circumferential rings or nodules 232. The provision of the circumferential rings 232 enhances surface area for the application of adhesive as discussed above with reference to the previous embodiments. With regard to the trailing end 228, barbs 234 are circumferentially positioned thereabout and enhance secure positioning within the vertebral bodies. The barbs 234 at the trailing end 228 of the stabilization device 210 are formed to face in opposite directions, ensuring secure placement of the stabilization devices 210 within the vertebral bodies. In addition, holes 235 are placed on the leading and trailing ends 226, 228 of the stabilization devices 210 to aid bony ingrowth or fixation with polymethylmethacrylate (PMMA), a bone filler or bioadhesive (example cyanoacrylate). As briefly discussed above, the stabilization device 210 has a predetermined curved shape determined so as to provide the greatest contact between the adjacent vertebral bodies and those skilled in the art will appreciate that variations are certainly possible without departing from the spirit of the present.

In accordance with yet another embodiment of the stabilization device, and with reference to FIG. 14, the stabilization device 310 includes a leading end 326 and a trailing end 328. The leading end 326 is preferably configured with a blunt or rounded tip 330. The leading end 326, just proximal to the tip 330, includes a series of circumferential rings or nodules 332. The provision of the circumferential rings 332 enhances surface area for the application of adhesive as discussed above with reference to the previous embodiments. With regard to the trailing end 328, barbs 334 are circumferentially positioned thereabout and enhance secure positioning within the vertebral bodies. The barbs 334 at the trailing end 328 of the stabilization device 310 are formed to face in opposite directions, ensuring secure placement of the stabilization devices 310 within the vertebral bodies. In addition, holes 335 are placed on the leading and trailing ends 326, 328 of the stabilization device 210 to aid bony ingrowth or fixation with polymethylmethacrylate (PMMA), a bone filler or bioadhesive (example cyanoacrylate).

In accordance with a further embodiment of the stabilization device, and with reference to FIG. 15, the stabilization device 410 includes a leading end 426 and a trailing end 428. The leading end 426 is preferably configured with a blunt or rounded tip 430. The leading end 426, just proximal to the tip 430, and the trailing end 428 respectively include a series of circumferential rings or nodules 432, 434. The provision of the circumferential rings 432, 434 enhances surface area for the application of adhesive as discussed above with reference to the previous embodiments. In addition, holes 435 are placed on the leading and trailing ends 426, 428 of the stabilization device 410 to aid bony ingrowth or fixation with polymethylmethacrylate (PMMA), a bone filler or bioadhesive (example cyanoacrylate).

In accordance with a further embodiment of the stabilization device, and with reference to FIGS. 16 and 17, the stabilization device 510 includes a leading end 526 and a trailing end 528. The leading end 526 is preferably configured with a tip 530 which may be sharp or blunt. The leading end 526 is further provided with a spring biased retaining wing(s) 536 which folds flush with the outer profile of the stabilization device 510 upon insertion (see FIG. 16). Upon slight proximal pulling of the stabilization device 510, the wing(s) 536 is biased outwardly to a substantially perpendicular orientation locking the stabilization device 510 in position (see FIG. 17). The leading end 526, just proximal to the tip 530, and the trailing end 428 respectively include a series of circumferential rings or nodules 532, 534. The provision of the circumferential rings 532, 534 enhances surface area for the application of adhesive as discussed above with reference to the previous embodiments. In addition, holes 535 are placed on the leading and trailing ends 526, 528 of the stabilization device 510 to aid bony ingrowth or fixation with polymethylmethacrylate (PMMA), a bone filler or bioadhesive (example cyanoacrylate).

In addition to the fixation technique disclosed above, it is contemplated the present stabilization device may be applied via a cervical application approach. In particular, and in accordance with this embodiment the introducer needle enters from the front of the patient and the stabilization device is also inserted from the front by a direct puncture of the antero-lateral cervical vertebral body. Once the introducer needle is positioned in the anterior one third of the vertebral body, the stabilization device is inserted in similar fashion as the lumbar application described above. As with the previously described lumbar approach, the procedure is repeated on the contralateral side and stabilization is achieved by placement of two to four stabilization devices.

In addition to the various techniques described above, methods for removal, retrieval and repositioning of the stabilization devices are further contemplated. In particular, and in accordance with a first embodiment 16, as shown in FIGS. 18 to 21, the pedicles of the vertebral bodies previously stabilized are accessed with an introducer needle positioned just beyond the posterior cortex of the vertebral bodies. Once properly positioned, the inner stylet of the introducer needle is removed and a curved shape memory or superelastic coring cannula 17 (slightly larger diameter than the stabilization rod) is advanced over the implanted stabilization device 10', separating the stabilization device 10' from bone ingrowth, PMMA or other bone cement. The coring cannula 17 is withdrawn (those skilled in the art will appreciate that the coring cannula step may not be required to extract the stabilization device). The introducer rod 22 is then advanced through the introducer needle 16 and adjoined to the stabilization device 10' by rotating clockwise or threading the stabilization device 10'. The introducer rod 22 and stabilization device 10' are withdrawn back through the introducer needle 16. In accordance with a preferred embodiment, the procedure is repeated on the remaining stabilization devices 10. Thereafter, repositioning of the stabilization devices may be performed in the manner discussed above.

In accordance with an alternate embodiment for removal, as shown in FIGS. 22 to 25, retrieval and repositioning of the stabilization devices, the pedicles of the vertebral bodies previously stabilized are accessed with an introducer needle 16 positioned just beyond the posterior cortex of the vertebral bodies. Once properly positioned, the inner stylet of the introducer needle 16 is removed and a curved shape memory or superelastic coring cannula 17 (slightly larger diameter than the stabilization device) is advanced over the implanted stabilization device 10', separating the stabilization device 10' from bone ingrowth, PMMA or other bone cement. The introducer rod 22 is advanced through the coring cannula 17 and introducer needle 16 and adjoined to the stabilization device 10' by rotating clockwise or threading the stabilization device 10'. The introducer rod 22, attached stabilization device 10' and coring cannula 17 are simultaneously withdrawn back through the introducer needle 16. In accordance with a preferred embodiment, the procedure is repeated on the remaining stabilization devices 10. Thereafter, repositioning of the stabilization devices may be performed in the manner discussed above.

While the preferred embodiments have been shown and described, it will be understood that there is no intent to limit the invention by such disclosure, but rather, is intended to cover all modifications and alternate constructions falling within the spirit and scope of the invention.

The invention claimed is:
1. A stabilization device for use with a system for the percutaneous stabilization of adjacent vertebrae, the stabilization device comprising:
   an elongated stabilization device body made of a shape memory or super elastic material which is substantially straight prior to deployment and takes a desired curved configuration upon entering the vertebrae;

the stabilization device body assuming a radius of curvature upon entering the vertebrae, the radius of curvature being between 3 cm and 6 cm and, encompassing an arc of 60° to 110°, the stabilization device further including a leading end and a trailing end, wherein the trailing end includes a keying element for ensuring proper orientation of the stabilization device during insertion, the stabilization device further includes rings, holes or barbs adjacent the trailing end and leading end for fixation with the vertebral body.

2. The stabilization device according to claim 1, wherein the leading end is pointed for penetration through a vertebral body.

3. The stabilization device according to claim 1, wherein the leading end is blunt.

4. The stabilization device according to claim 1, wherein the leading end includes at least one circumferential ring.

5. The stabilization device according to claim 1, wherein the trailing end includes at least one circumferential ring.

6. The stabilization device according to claim 1, further including barbs adjacent the trailing end and leading end for fixation with the vertebral body.

7. The stabilization device according to claim 1, wherein the respective barbs at the respective leading end and trailing end of the stabilization device are formed to face in opposite directions ensuring secure placement of the stabilization device.

8. The stabilization device according to claim 1, wherein the stabilization device body is tubular.

9. The stabilization device according to claim 1, wherein the stabilization device body includes and inner, stabilization member timed and inserted coaxially inside an outer stabilization member.

10. The stabilization device according to claim 7, further including holes positioned adjacent the trailing end and the leading end of the stabilization device, the holes being shaped and dimensioned for encouraging bony ingrowth.

11. The stabilization device according to claim 1, further including holes positioned adjacent the trailing end and the leading end of the stabilization device, the holes being shaped and dimensioned for encouraging bony ingrowth.

12. The stabilization device according to claim 11, wherein the stabilization device body is tubular and permits the passage of an adhesive therethrough and into the holes for encouraging fixation within the vertebral bodies.

13. A method for the percutaneous stabilization of adjacent vertebral bodies, comprising:
inserting an elongated stabilization device within the vertebrae such that it extends between adjacent vertebral bodies to securely stabilize the adjacent vertebral bodies, the stabilization device including an elongated stabilization device body, the stabilization device body being made of a shape memory or super elastic material which is substantially straight prior to deployment and takes a desired curved configuration upon entering the vertebrae such that the stabilization device body assumes a radius of curvature upon entering the vertebrae, the radius of curvature being between 3 cm and 6 cm and, encompassing an arc of 60° to 110°, the stabilization device further including a leading end and a trailing end wherein the trailing end includes a keying element for ensuring proper orientation of the stabilization device during insertion; and retrieving the elongated stabilization device from its position within the vertebrae.

14. The method according to claim 13, wherein the stabilization device is substantially cylindrical in cross section, and the leading end and a trailing end wherein the leading end is pointed for penetration through a vertebral body.

15. The method according to claim 13, further including the step of inserting a plurality of elongated stabilization devices within the vertebrae such that they extend between adjacent vertebral bodies to securely stabilize the adjacent vertebral bodies.

16. The method according to claim 15, wherein at least four stabilization devices are inserted.

17. The method according to claim 13, further including the step of inserting an introducer needle within one of the adjacent vertebral bodies prior to insertion of the stabilization device, wherein the stabilization device is inserted through the introducer needle.

18. The method according to claim 17, wherein the step of inserting includes releasably securing the stabilization device to an introducer rod and using the introducer rod to force the stabilization device through the adjacent vertebral bodies during insertion.

19. The method according to claim 18, wherein threading respectively formed along the trailing end of the stabilization device and the introducer rod releasably secures the stabilization device to the introducer rod.

20. The method according to claim 13, wherein the stabilization device includes barbs adjacent the trailing end for fixation with the vertebral body.

21. The method according to claim 13, wherein the step of inserting includes securing the stabilization device to an introducer rod and using the introducer rod to force the stabilization device through the adjacent vertebral bodies during insertion.

22. The method according to claim 21, wherein the introducer rod is releasably secured to the trailing end of the stabilization device.

23. The method according to claim 22, wherein threading respectively formed along the trailing end of the stabilization device and the introducer rod releasably secures the stabilization device to the introducer rod.

* * * * *